United States Patent [19]

Gammill

[11] Patent Number: 4,459,420

[45] Date of Patent: Jul. 10, 1984

[54] PYROGALLOL SYNTHESIS OF ANTI-ATHEROGENIC FUROCHROMONES

[75] Inventor: Ronald B. Gammill, Portage, Mich.

[73] Assignee: The Upjohn Company, Kalamazoo, Mich.

[21] Appl. No.: 378,686

[22] Filed: May 17, 1982

[51] Int. Cl.$^3$ ............................................ C07D 307/79
[52] U.S. Cl. .................................... 549/471; 549/387; 549/470
[58] Field of Search ................................ 549/387, 471

[56] References Cited

U.S. PATENT DOCUMENTS 2,680,119  6/1954  Robertson et al. ................. 549/387
4,284,569  8/1981  Gammill ............................ 549/387

OTHER PUBLICATIONS

Brother et al., Helv. Chim. Acta, 35, 9, (1952).
Taylor, J. Org. Chem., 41, 282, (1976).
R. Aneja, et al., A New Synthesis of Khellin, J. Sci. Industr. Res., 17B:382–383, (1958).
R. Aneja, et al., Neue Synthesen von Khellin, Chem. Ber., 93:297–303, (1960).
R. A. Baxter, et al., Furochromones. Part I. The Synthesis of Khellin, J. Chem. Soc., pp. S30–S33, (1949).
J. R. Clarke, et al., Furano-compounds. Part IX. The Synthesis of Kellin and Related Compounds, J. Chem. Soc., pp. 302–307, (1949).
O. Dann, et al., Eine Neue Synthese von Khellin und Anderen Furo-2-Methyl-Chromonen, Ann. Chem., 605:146–157, (1957).
O. Dann, et al., Synthese von 2-Methyl-5.8-dihydroxy-furano-[3'.2':6.7]-Chromon und von Khellin, Chem. Berg., 93:2829–2833, (1960).
T. S. Gardner, et al., The Synthesis of Khellin Derivatives, J. Org. Chem., 15:841–849, (1950).
T. A. Geissman, et al., Chromones. III. A Total Synthesis of Khellin, J. Amer. Chem. soc., 73:1280–1284, (1951).
V. V. S. Murti, et al., A Synthesis of Kellin, J. Sci. Ind. Res., (India), 8B:112–113, (1949).
V. V. S. Murti, et al., Nuclear Oxidation in Flavones and Related Compounds, Part XXIII., Proc. of the Indian Acad. of Sci., 30A:107–113, (1949).
C. Musante, Prodotti di scissione alcalina della Khellina e loro derivati e trasformazione del sistema del furo--cromone in quello del furo–benzo-isossazolo, Gazz. Chim. Ital., 88:910–929, (1958).
L. R. Row, et al., Furanobenzopyrones: Part VII, Indian J. Chem., 5:105–106, (1967).
A. Schonberg, et al., Khellin from Visnagin, J. Amer. Chem. Soc., 73:2960–2961, (1951).
E. Spath, et al., Die Konstitution des Kellins, Chem. Ber., 71:106–113, (1938).

Primary Examiner—Nicky Chan
Attorney, Agent, or Firm—Lawrence T. Welch; Robert A. Armitage

[57] ABSTRACT

The present invention provides a total synthesis of known intermediates useful in the synthesis of khellin and antiatherosclerotic analogs thereof from pyrogallol. Pyrogallol is converted to 3,6,7-benzofurantriol triacetate using zinc chloride and chloracetanitrile, then catalytically reduced and deactoxylated at the 3 position to yield the corresponding 2,3-dihydrofuran. This substance is subjected to a Fries rearrangement to the corresponding diol, the phenolic hydroxyl group of which is then selectively alkylated. This yields 6-hydroxy-7-alkoxy-5-benzofuranyl methyl ketone, a known intermediate for the production of 4-desmethoxy khellin and analogs thereof. This compound is then selectively alkoxylated at the 4 position using lead tetraacetate or thallium (III) nitrate in an alkanol solvent to yield known chemical intermediates in the preparation of khellin and analogs thereof.

1 Claim, No Drawings

PYROGALLOL SYNTHESIS OF ANTI-ATHEROGENIC FUROCHROMONES

BACKGROUND OF THE INVENTION

The present invention provides novel compositions of matter and processes for their preparation. Particularly, the present invention relates to novel chemical intermediates and associated processes for the preparation of furochromones. Most especially, the present invention provides for the preparation of novel antiatherosclerotic furochromones, particularly khellin analogs.

Khellin and related compounds are known to exert a wide variety of pharmacological effects. Recently, khellin has been reported to exhibit useful antiatherosclerotic activities. Moreover, numerous analogs of khellin likewise are known to exert useful antiatherosclerotic effects. For example, 7-methylthiomethyl-4,9-dimethoxyfurochromone is described in U.S. Pat. No. 4,284,569 as such a useful antiatherosclerotic substance.

Methods for the total synthesis of khellin are known. For example, pyrogallol has been employed as a starting material for the synthesis of furochromones such as khellin. See Clarke, J. R., et al., J. Chem. Soc., 302 (1949), Baxter, R. A., et al., J. Chem. Soc., S30 (1949), Schonberg, A., et al., J. Am. Chem. Soc., 73: 2960 (1951), Murti, V. V. S., et al., Proc. of the Indian Acad. of Sci., 30A: 107 (1949), and Geissman, T. A., et al., J. Am. Chem. Soc., 73: 1280 (1951). Also descriptive of the synthesis of khellin are Spath, E., et al., Chem. Ber., 71: 106 (1938), Dann, O., et al., Chem. Ber., 83: 2829 (1960), Dann, O., et al., Ann. Chem., 605: 146 (1957), and Murti, V. V. S., et al., J. Sci. Ind. Res. (India), 8B: 112 (1949). See also U.S. Pat. No. 2,680,119 describing the synthesis of khellin and related compounds.

Other references describing the synthesis of intermediates useful in the preparation of khellin for analogs include: Aneja, R., et al., Chem. Ber., 93: 297 (1960), Aneja, R., et al., J. Sci. Ind. Res. (India), 17B: 382 (1958), Gardner, T. S., et al., J. Org. Chem., 15: 841 (1950), and Rowe, L. R., et al., Indian J. Chem., 5: 105 (1967).

Accordingly, the references cited above describe the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by Musante, C., Gazz. Chim. Ital., 88: 910 (1958).

PRIOR ART

Methods of the total synthesis of khellin are known, as are certain chemical intermediates useful in its synthesis.

The use of pyrogallol in the synthesis of khellin intermediates is known. For example, the transformation of pyrogallol to the khellin intermediate 1-(2,3-dihydro-6,7-dihydroxy-5-benzofuranyl)ethanone is known. The parahydroxylation of this intermediate is also known. See Row, L. R., et al., Indian J. Chem., 5: 105 (1967) describing this transformation and the subsequent dimethylation to yield known khellin intermediates. U.S. Pat. No. 4,284,569 provides a variety of novel anti-atherosclerotic furochromones.

SUMMARY OF THE INVENTION

The present invention particularly provides:

(a) A method of preparing a dialkoxybenzofuran of formula I, wherein $R_2$ and $R_3$ are $C_1$-$C_4$ alkyl, being the same or different, which comprises para-alkoxylating a mono-alkoxybenzofuran of formula II, wherein $R_2$ is as defined above, with an oxidizing reagent selected from the group consisting of
  (i) thallium (III) nitrate,
  (ii) ceric ammonium nitrate,
  (iii) lead tetraacetate,
in a $C_1$-$C_4$ alkanol solvent of the formula $R_3OH$,
  wherein $R_3$ is as defined above;
(b) A benzofuran of formula III,
  wherein $R_2$ is $C_1$-$C_4$ alkyl;
(c) A benzofuran of formula IV,
  wherein $R_5$ is $C_2$-$C_4$ alkyl;
(d) A benzofuran of formula V,
  wherein one of $R_6$ and $R_7$ is $C_1$-$C_4$ alkyl and the other is $C_2$-$C_4$ alkyl with the proviso that $R_6$ and $R_7$ are different;
(e) An anti-atherosclerotic furochromone of formula VI,
  wherein $R_6$ and $R_7$ are as defined above;
  wherein $R_{12}$ is:
  (1) hydrogen;
  (2) $C_1$-$C_8$ alkyl;
  (3) $C_2$-$C_8$ alkoxymethyl;
  (4) $C_2$-$C_8$ alkylthioalkyl;
  (5) trifluoromethyl;
  (6) phenoxymethyl optionally substituted by chloro, fluoro, trifluoromethyl, $C_1$-$C_3$ alkyl or $C_1$-$C_3$ alkoxy;
  (7) phenylthiomethyl optionally substituted by chloro, fluoro, trifluoromethyl, $C_1$-$C_3$ alkyl or $C_1$-$C_3$ alkoxy;
  (8) —$CH_2$—$S(O)_n$—$R_{20}$, wherein n is zero, one or 2 and $R_{20}$ is $C_1$-$C_5$ alkyl; or
  (9) —$CH_2NR_8R_9$, wherein $R_8$ and $R_9$ are hydrogen, $C_1$-$C_{12}$ alkyl or wherein $R_8$ and $R_9$, taken together with N, form a saturated or unsaturated heterocyclic amine ring consisting of from 2 to 7 carbon atoms, inclusive, and zero, one, or 2 additional hetero atoms, with the proviso that said heterocyclic amine ring contains 4 to 8 atoms in the ring, said additional hetero atoms being selected from the group consisting of oxygen, nitrogen, and sulfur, said heterocyclic amine ring being optionally substituted by $C_1$-$C_4$ alkyl, $C_2$-$C_8$ alkylthiomethyl or alkoxymethyl $C_1$-$C_4$ hydroxyalkyl, or phenyl;
  wherein $R_{13}$ is:
  (1) hydrogen;
  (2) chloro, iodo, or bromo; or
  (3) —$CH_2$—$S(O)_n$—$R_{20}$ wherein n and $R_{20}$ are as defined above, with the proviso that $R_{13}$ is —$CH_2$—$S(O)_n$—$R_{20}$ only when $R_{14}$ is methyl;
(f) 4-Ethoxy-9-methoxy-7-methylthiomethylfurochromone; and
(g) 4-Methoxy-9-ethoxy-7-methylthiomethylfurochromone.

In accordance with the method described above, there is prepared the formula II alkoxybenzofuran. This formula II alkoxybenzofuran wherein $R_2$ is methyl is known to be useful in the preparation of a wide variety of anti-atherosclerotic substances, including khellin and various analogs thereof. See U.S. Pat. No. 4,284,569.

Similarly there are prepared the novel formula XI benzofurans when $R_1$ is $C_2$-$C_4$ alkoxy. These intermediates are useful in the preparation of novel anti-atherosclerotic 4,9-di-($C_2$-$C_4$)-alkoxyfurochromones of formula VIII by means described in U.S. Pat. No. 4,284,569 for the preparation of the corresponding 4,9-dimethoxyfurochromones therein. Moreover, the manner of use of the novel 4,9-di-($C_2$–$C_4$)-alkoxy-furochromones of formula VIII in the treatment and prevention of atherosclerosis is the same as that described in U.S. Pat. No. 4,284,569 for the corresponding 4,9-dimethoxy compounds. Accordingly, the manner of the preparation and pharmacological use of these novel formula VIII compounds is incorporated herein by and reference from the description of the preparation and use in U.S. Pat. No. 4,284,569 of the antiatherosclerotic 4,9-dimethoxyfurochromones. Among the novel formula VIII compounds herein, the 4,9-diethoxyfurochromones are preferred.

The process of the present invention is more completely understood by reference to the charts below. In these charts, $R_1$ is hydrogen or $C_1$–$C_4$ alkyloxy or hydrogen. $R_2$, $R_3$, $R_{12}$ and $R_{13}$ are as defined above.

$R_{11}$ is:
(a) hydrogen;
(b) $C_1$–$C_8$ alkyl;
(c) $C_2$–$C_8$ alkoxymethyl;
(d) $C_2$–$C_8$ alkylthioalkyl;
(e) trifluromethyl;
(f) phenoxymethyl;
(g) phenylthiomethyl;
(h) phenoxymethyl or phenylthiomethyl, either of which is optionally substituted by one chloro, fluoro, trifluoromethyl, $C_1$–$C_3$-alkyl, or $C_1$–$C_3$-alkoxy; or
(i) $C_3$–$C_{10}$ cycloalkyl.

The carbon atom content of various hydrocarbon containing moities is indicated by a prefix designating the minimum and maximum number of carbon atoms in the moiety, i.e., the prefix $C_i$–$C_j$ indicates a carbon atom content of the integer "i" to the integer "j" carbon atoms, inclusive. Thus, $C_1$–$C_3$ alkyl refers to alkyl of 1–3 carton atoms, inclusive, or methyl, ethyl, propyl, and isopropyl.

With respect to the charts, Chart A provides a method whereby the known formula XXI compound is transformed to the novel formula XXV 2,3-dihydrobenzofuran, which is in turn reduced to the known formula XXVI benzofuran intermediate for preparing desmethoxy khellin and other khellin analogs.

With further respect to Chart A, pyrogallol is converted to the formula XXII triacetate first by treatment with chloroacetonitrile according to procedures described by Geissman, T. A., et al., J. Amer. Chem. Soc., 73: 57–65 (1951).

Thereafter the formula XXIII production product is obtained from the formula XXII compound employing a metal catalyst under a hydrogen atmosphere. For example, conventional metal catalysts such as palladium and carbon catalysts are employed. See Dann, O. and Zeller, H. G., Ber. 93: 28–29 (1960) for a transcription of this transformation.

Thereafter the formula XXIII compound then to go to Fries rearrangement to yield formula XXIV dihydroxy ketone. By this procedure, the formula XXIII compound is treated with a mixture of aluminium trichloride and nitrobenzene.

This formula XXIV compound is then selectively $C_1$–$C_4$ alkylated to the formula XXV compound by treatment with an alkyl iodide. Any concomitant desalkoxylation in this reaction is reversed by treatment with hydrobromic acid.

This novel formula XXV compound is then dehydrogenated using 2,3-dichloro-5,6-dicyanobenzoquinone (DDQ). See Linn, Y. Y., et al., J. Heterocyclic Chem., 799 (1979).

The formula XXVI compound thusly prepared is a highly useful intermediate in the synthesis of analogs of khellin, specifically the 4-desmethoxy khellin. See, for example, U.S. Pat. No. 4,284,569, describing the synthesis of such analogs from the formula XXVI compound wherein $R_2$ is methyl.

With respect to Chart B, a method is provided for the paraalkoxylation of the formula XXXI compound, prepared as the formula XXVI compound in Chart A. This methoxylation preceeds by the use of an oxidizing agent in a $C_1$–$C_4$ alkanol solvent corresponding to the alkoxy group to be introduced at $C_4$. Pb(OAc)$_4$ may be employed as the oxidizing agent. See Brother, A. E., et al., Helv. Chim. Acta., 35: 9–10 (1952). Alternatively, however, thallium (III) nitrate is employed as the oxidizing agent. See Taylor, E. C., J. Organic Chem., 41: 282 (1976). In the latter case, maximum yields are obtained when the oxidizing agent is added over a period of about 15 min with the reaction mixture being maintained at about $-25°$ C. for 30 min followed by heating for 1–2 min.

Chart C provides an illustration of the method by which the formula XLI compound, prepared as the formula XXVI compound of Chart A or the formula XXXII compound of Chart B, is transformed to khellin 4-desmethoxy khellin or analogs thereof. Procedures of Chart C are, for example, known in the art from U.S. Pat. No. 4,284,569 wherein Chart A of that patent describes the synthesis of the various formula XLII and formula XLIII compounds from the formula XLI starting material. Accordingly, the charts herein provide a description of the preparation and use of the novel process and compounds of the present invention.

DESCRIPTION OF THE PREFERRED EMBODIMENTS

The present disclosure is more fully understood by the operation of the following examples:

EXAMPLE 1

3,6,7-Benzofurantriol triacetate (Formula XXII)

Refer to Chart A

Dry zinc chloride (38 g) is added to pyrogallol (Formula XXII, 35 g). To these solids under a nitrogen atmosphere is added diethyl ether and chloroacetonitrile (18 ml). The resulting mixure is then stirred and cooled to 0° C. Hydrochloride gas is then bubbled to the reaction mixture for 30 min, the mixture is allowed to warm slowly to ambient temperature with stirring for 12 hr. Thereafter, the two-face mixture is cooled to 0° C. and the ether layer decanted. Additional diethyl ether (100 mg) is added, stirred, and decanted. Water (250 ml) is added to the resulting residue and the aqueous mixture is then refluxed for 30 min yielding a homogeneous solution. The solution is then cooled to 4° C., filtered, and yields a reddish-brown solid (24.5 g), α-chlorogallacetophenone. Without further purification, the solid is then dissolved in ethanol (300 ml) containing sodium acetate (24.5 g). After refluxing for 5 hr, the resulting mixture is then dried and treated with acetic anhydride (150 ml) and pyridine (75 ml). The resulting mixture is then stirred at ambient temperature for 12 hr, decanted into ice water (700 ml) and stirred for one hr.

The resulting precipitate is then collected on a filter, washed with water and air dried. Thereafter, the filtrate is acidified with coconcentrated hydrochloric acid and extracted with ethyl acetate. The organic extracts are then washed thoroughly with saturated sodium bicarbonated brine, dried over magnesium sulphate, and concentrated to a residue. Chromatography on 1.3 kg of silica gel alluding with 40% ethyl acetate Skellysolve B ethyl acetate to obtain 27.75 g of pure product, a white solid, melting point 99°–101° C.

EXAMPLE 2

2,3-Dihydro-6,7-benzofurandiol diacetate (Formula XXIII)

A mixture of the title product of Example 1 (50 g) in ethyl acetate (350 ml) is treated with anhydrus potassium acetate (7.5 g) and 7.5 g of a 10% paladium on carbon catalyst. The reaction mixture is then hydrogenated at 65° C. for 2 hr, cooled to ambient temperature, and filtered through diaconaceous earth. The resulting filtrate is then concentrated under reduced pressure yielding a solid. Recrystallization from 250 ml of ethyl acetate and Skellysolve B (1:1) yields 33.65 g of pure title product as a white solid, melting point 114°–115° C. Silica gel TLC $R_f$ is 0.31 in 25% ethyl acetate in hexane. IR absorptions (cm$^{-1}$) are observed at 1765, 1625, 1610, 1490, 1465, 1375, 1225, 1210, 1180, and 1035. NMR absorptions are observed at 7.05, 6.62, 4.64, 3.21, 2.25, and 2.23 δ.

EXAMPLE 3

1-(2,3-dihydro-6,7-dihydroxy-5-benzofuranyl)-ethanone (Formula XXIV)

Refer to Chart A

A mixture of the title product of Example 2 (9.50 g), nitrobenzene (100 ml) and aluminium trichloride (6.36 g) is heated at 60° C. for 90 min. After cooling to ambient temperature, the reaction mixture is poured over ice and 2N hydrochloric acid (100 ml) is added, followed by the addition of water (300 ml). After stirring for 3 hr, the reaction mixture is then extracted with ethyl acetate. The organic layer is then separated and washed with 5% aqueous sodium hydroxide and the aqueous layer then poured into 2N hydrochloric acid (500 ml), yielding a precipitate. Ethyl acetate is then added and then separated from the aqueous layer. The organic layer is then dried over magnesium sulphate and concentrated under reduced pressure to yield 6.35 g of title product as a brown solid. Recrystallization from ethyl acetate yields pure crystalline product, melting point 190°–190.5° C. Silica gel TLC $R_f$ is 0.25 in 5% ethyl acetate in trichloromethane. IR absorptions (cm$^{-1}$) are observed at 3460, 3200, 1645, 1605, 1490, 1445, 1365, 1320, 1255, and 1055. NMR absorptions are observed at 7.15, 4.70, 3.18, and 2.52 δ.

EXAMPLE 4

1-(2,3-dihydro-6-hydroxy-7-methoxy-5-benzofuranyl)-ethanone (Formula XXV: R$_2$ is methyl)

Refer to Chart A

A mixture of the title product of Example 3 (5.9 g) potassium carbonate (12 g) and methyl iodide (25 g) is heated at reflux and acetone for 18 hr. After cooling to ambient temperature and removal of the potassium carbonate by filtration, the resulting mixture is then concentrated under reduced pressure to a yellow oil. The oil is then dissolved in trichloromethane and treated with hydrobromic acid and refluxed for 2 hr. After cooling to ambient temperature and concentration under reduced pressure, chromatography eluting with 5% ethyl acetate in trichloromethane yields 6.0 g of pure title product, melting point 95°–97° C. Silica gel TLC $R_f$ is 0.5 in 5% ethyl acetate in trichloromethane. IR absorptions (CM$^{-1}$) are observed at 2700, 1630, 1615, 1430, 1405, 1365, 1330, 1290, and 1060. NMR absorptions are observed at 7.3, 6.48, 3.9, and 3.15 δ.

EXAMPLE 5

1-(6-hydroxy-7-methoxy-5-benzofuranyl)-ethanone (Formula XXVI: R$_2$ is methyl)

Refer to Chart A

To a solution of the title product of Example 4 (12.1 g) in dioxane is added 2,3-dichloro-5,6-dicyanobenzoquinone (DDQ, 17.8 g). The resulting black solution is then stirred at reflux for 2 hr. Upon cooling to ambient temperature, a precipitate forms. The reaction mixture is then filtered and the filter cake is washed with dichloromethane. The filtrate is then concentrated to a residue and the residue chromatographed on 700 g of silica gel eluting with dichloromethane. Pure title product is obtained as 5.5 g of an oil which spontaneously crystallizes. Recrystallization from ethyl acetate in hexane (1:5) yields pure title product, melting point 61.2°–63.5° C. Silica gel TLC $R_f$ is 0.31 in 25% ethyl acetate in hexane. IR absorptions (CM$^{-1}$) are observed at 3140, 3110, 2720, 1635, 1625, 1545, 1320, 1300, 1275, and 1050. NMR absorptions are observed at 7.78, 7.65, 4.21, and 2.71 δ.

EXAMPLE 6

1-(6-hydroxy-4,7-dimethoxy-5-benzofuranyl)-ethanone (Formula XXXII: R$_2$ and R$_3$ are both methyl)

Refer to Chart B

A. The title product of Example 5 (100 mg) is added to methanol (4 ml) and cooled to −25° C. To the resulting heterogeneous mixture is added a methanolic (7 ml) solution of thallium (III) nitrate trihydrate, TL (ONO$_2$)$_3$.3H$_2$O (250 mg), dropwise over about 15 min. The resulting mixture is then stirred for 30 min at −25° C. and heated to reflux for 1–2 min. The reaction is then poured into saturated aqueous sodium bicarbonate and extracted with diethyl ether. The ethereal layer is then dried over magnesium sulphate and concentrated under reduced pressure to yield a yellow oil. Crystallization is achieved by dissolving the oil in 1% ethyl acetate in hexane and cooling to 0° C. for 12 hr. Filtration of the resulting crystals yields 70 mg of pure title product, melting point 98°–99° C. Silica gel TLC $R_f$ is 0.6 in ethyl acetate at hexane (1:1). IR absorptions (CM$^{-1}$) are observed at 2955, 2930, 2926, 2868, 1629, 1619, 1587, 1471, 1452, 1444, 1425, 1382, 1364, 1303, 1267, 1151, 1079, 1061, and 755. NMR absorptions are observed at 7.5, 6.9, 4.15, 4.05, and 2.78.

B. Alternatively title product is prepared utilizing lead tetraacetate (200 mg) which is added to methanol (6 ml) and cooled to 0° C. To the resulting solution is added the title product of Example 5 (100 mg) dropwise in methanol (5 ml). The resulting mixture is then stirred at 0° C. for 80 min and poured into saturated aqueous sodium bicarbonate. After extraction with ether, the ethereal solution is then dried over magnesium sulphate and concentrated under reduced pressure to yield a yellow oil. This crude solid is then dissolved in methanol and heated at reflux for 1 hr. After cooling to ambient temperature and removal of solvent under reduced pressure, crystallization from 1% ethyl acetate in hexane yields 70 mg of pure title product, melting point 98°–100° C.

EXAMPLE 7

7-Methylthiomethiomethyl-7-methoxy-9-ethoxy-furochromone (Formula XXIII: $R_1$ is methyl, $R_2$ is ethyl, $R_{12}$ is methylthiomethyl, and $R_{13}$ is hydrogen)

Refer to Charts A, B, and C

A. A mixture of the title product of Example 3 (5.9 g) potassium carbonate (12 g) and ethyl iodide (28 g) is heated at reflux and acetone for 18 hr. After cooling to ambient temperature and removal of the potassium carbonate by filtration, the resulting mixture is then concentrated under reduced pressure. The residue is then dissolved in trichloromethane and treated with hydrobromic acid and refluxed for 2 hr. After cooling to ambient temperature and concentration under reduced pressure, chromatography eluting with 5% ethyl acetate in trichloromethane yields 6.0 g of formula XXV product.

B. To a solution of the product of Part A (12 g) in dioxane is added 2,3-dichloro-5,6-dicyanobenzoquinone (DDQ, 17.8 g). The resulting black solution is then stirred at reflux for 2 hr. Upon cooling to ambient temperature, a precipitate forms. The reaction mixture is then filtered and the filter cake is washed with dichloromethane. The filtrate is then concentrated to a residue and the residue chromatographed on 700 g of silica gel eluting with dichloromethane to obtain formula XXVI product, 1-(6-hydroxy-7-ethoxy-5-benzofuranyl)-ethanone.

C. The formula XXVI product of Part B (100 mg) is added to methanol (4 ml) and cooled to −25° C. To the resulting mixture is added a methanolic (7 ml) solution of thallium (III) nitrate trihydrate, TL $(ONO_2)_3.3820$ (250 mg), dropwise over about 15 min. The resulting mixture is then stirred for 30 min at −25° C. and heated to reflux for 1–2 min. The reaction is then poured into saturated aqueous sodium bicarbonate and extracted with diethyl ether. The etheral layer is then dried over magnesium sulphate and concentrated under reduced pressure to yield formula XXXII product, 1-(6-hydroxy-4-methoxy-7-ethoxy-5-benzofuranyl)-ethanone.

D. To sodium hydride (20.1 g of a 50% dispersion in oil) and tetrahyrofuran (20 ml freshly distilled from lithium aluminum hydride), combined under a nitrogen atmosphere to form a slurry, are added dropwise a mixture of the product of Part C (56 g), ethyl 2-(methylthio)-acetate (26.4 g) and dry tetrahydrofuran (50 ml). After the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an aqueous layer which is diluted with methanol (100 ml) and concentrated hydrochloric acid (75 ml). This mixture is then refluxed for 45 min and thereupon allowed to cool to ambient temperature. Upon extraction with methylene chloride (600 ml) the organic extracts are dried and concentrated under reduced pressure to yield pure title product.

EXAMPLE 8

7-Methylthiomethiomethyl-4-ethoxy-9-methoxyfurochromone (Formula XXIII: $R_1$ is ethyl, $R_2$ is methyl, $R_{12}$ is methylthiomethyl, and $R_{13}$ is hydrogen)

Refer to Chart A, B, and C

A. The title product of Example 5 (100 mg) is added to ethanol (4.5 ml) and cooled to −25° C. To the resulting mixture is added an ethanolic (8 ml) solution of thallium (III) nitrate trihydrate, TL $(ONO_2)_3.3820$ (250 mg), dropwise over about 15 min. The resulting mixture is then stirred for 30 min at −25° C. and heated to reflux for 1–2 min. The reaction is then poured into saturated aqueous sodium bicarbonate and extracted with diethyl ether. The etheral layer is then dried over magnesium sulphate and concentrated under reduced pressure to yield formula XXXII product, 1-(6-hydroxy-4-ethoxy-7-methoxy-5-benzofuranyl)-ethanone.

B. To sodium hydride (20.1 g of a 50% dispersion in oil) and tetrahydrofuran (20 ml freshly distilled from lithium aluminum hydride), combined under a nitrogen atmosphere to form a slurry, are added dropwise a mixture of the product of Part A (56 g), ethyl 2-(methylthio)-acetate (26.4 g) and dry tetrahydrofuran (50 ml). After the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an aqueous layer which is diluted with methanol (100 ml) and concentrated hydrochloric acid (75 ml). This mixture is then refluxed for 45 min and thereupon allowed to cool to ambient temperature. Upon extraction with methylene chloride (600 ml) the organic extracts are dried and concentrated under reduced pressure to yield pure title product.

C. Alternatively title product is prepared as follows:

(1) 4,7-Dimethoxy-7-[(methylthio)methyl]-furochromone (15 g) is added to trichloromethane (250 ml). Anhydrous hydrobromic acid is then bubbled through the resulting mixture until a dark red color develops. The reaction is then heated to reflux for 45 min, cooled to ambient temperature, and diluted with water (200 ml). The organic layer is then separated, dried over magnesium sulphate, and concentrated under reduced pressure to yield 13.36 g of 4-hydroxy-7-[(methylthio)-methyl]-9-methoxy-furochromone. Melting point 134°–135° C.

(2) The product of part C(1) (4.0 g) is added to acetone (100 ml), ethyl iodide (15 ml) and potassium carbonate (9 g). The resulting mixture is then heated to reflux for 18 hr, cooled to ambient temperature, and concentrated under reduced pressure. The resulting solid is then washed with trichloromethane and separated by filtration. Concentration under reduced pressure yields a dark oil which is chromatographed on 300 gr of silica gel by high pressure liquid chromatography. Packing in elution with 10% ethyl acetate in trichloromethane yields 3.0 g of title product, melting point 112°–114° C. Silica gel TLC Rf is 0.78 in 1% methanol in ethyl acetate. IR absorptions ($cm^{-1}$) are observed at 3120, 1650, 1610, 1380, 1340, 1210, 1170, and 1065. NMR absorptions are observed at 7.62, 6.97, 6.15, 4.21, 4.20, 4.57, and 2.218.

FORMULAS
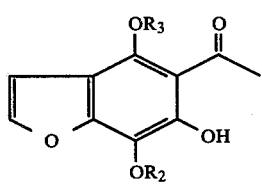 I
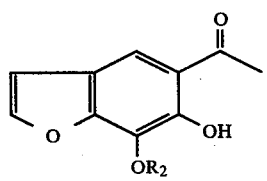 II
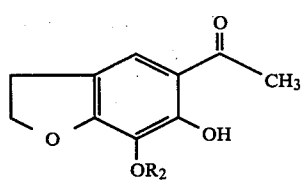 III
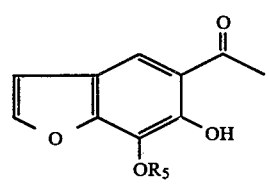 IV
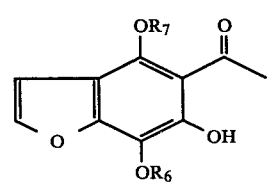 V
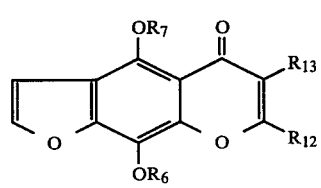 VI
CHART A
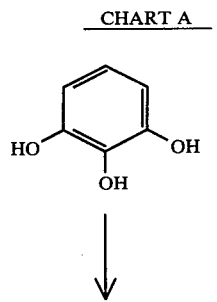 XXI
-continued
CHART A
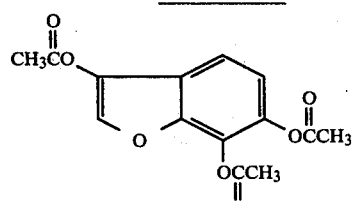 XXII
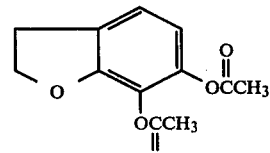 XXIII
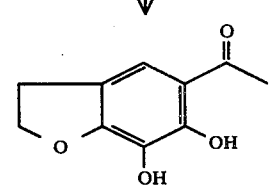 XXIV
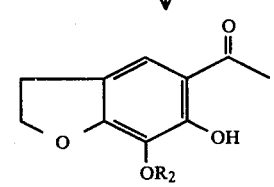 XXV
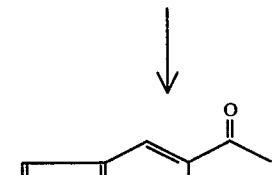 XXVI
CHART B
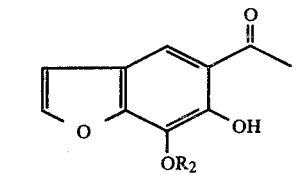 XXXI

-continued
CHART B

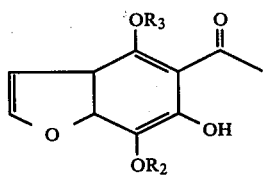

CHART C

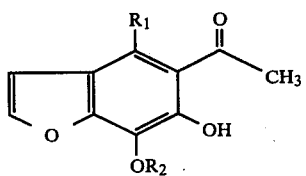

↓

↓

-continued
CHART C

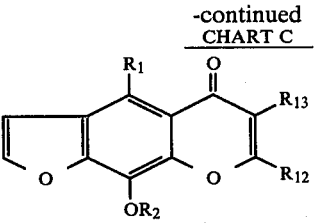 XLIII

I claim:
1. A method of preparing a dialkoxybenzofuran of formula I:

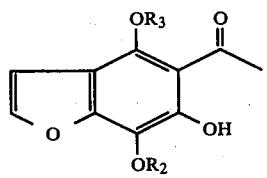 I

XLI wherein $R_2$ and $R_3$ are $C_1$–$C_4$ alkyl, being the same or different, which comprises:
para-alkoxylating a mono-alkoxybenzofuran of formula II

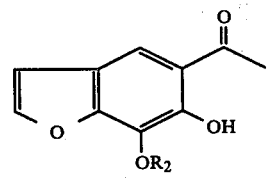 II

XLII wherein $R_2$ is as defined above, with an oxidizing reagent selected from the group consisting of:
(a) thallium (III) nitrate, or
(b) lead tetraacetate in a $C_1$–$C_4$ alkanol solvent of the formula $R_3OH$,
wherein $R_3$ is as defined above.

* * * * *